United States Patent [19]

White

[11] Patent Number: 5,512,039
[45] Date of Patent: Apr. 30, 1996

[54] MULTI-ANGLE KNEE SUPPORT

[76] Inventor: Patrick J. White, 6912 Ammons St., Arvada, Colo. 80004

[21] Appl. No.: 368,973

[22] Filed: Jan. 5, 1995

[51] Int. Cl.⁶ .................................................. A61F 5/00
[52] U.S. Cl. ............................. 602/26; 602/62; 602/63
[58] Field of Search ......................... 602/23, 26, 61–63

[56] References Cited

U.S. PATENT DOCUMENTS

| | | | |
|---|---|---|---|
| 3,046,981 | 7/1962 | Biggs, Jr. et al. | 602/26 |
| 3,934,583 | 1/1976 | Hollingshead et al. | 602/62 |
| 4,805,606 | 2/1989 | McDavid, III | 602/26 |
| 4,854,308 | 8/1989 | Drillio | 602/26 X |
| 5,016,621 | 5/1991 | Bender | 602/26 |

FOREIGN PATENT DOCUMENTS 8801855  3/1988  WIPO ........................................ 602/26

*Primary Examiner*—Linda C. Dvorak

[57] ABSTRACT

A multi-angle knee support comprising an upper adjustment sleeve fabricated of a flexible elastic plastic material, the upper sleeve being fabricated in a loop configuration with free ends, pile fasteners secured to the free ends of the upper sleeve; a lower adjustment sleeve fabricated of an flexible elastic plastic material, the lower sleeve being fabricated in a loop configuration with free ends, pile fasteners secured to the free ends of the lower sleeve; and a plurality of ligament imitation strips coupled between the upper and lower sleeves.

3 Claims, 4 Drawing Sheets

MULTI-ANGLE KNEE SUPPORT

BACKGROUND OF THE INVENTION

1. Field of the Invention

The present invention relates to multi-angle knee supports and more particularly pertains to providing physical support to the knee of a wearer in a manner to simulate the support normally provided through ligaments.

2. Description of the Prior Art

The use of devices to be worn at the joint of a person to provide physical support to the joint is known in the prior art. More specifically, devices to be worn at the joint of a person to provide physical support to the joint heretofore devised and utilized for the purpose of providing support to the weakened joint of a wearer through any number of a wide variety of devices are known to consist basically of familiar, expected, and obvious structural configurations, notwithstanding the myriad of designs encompassed by the crowded prior art which has been developed for the fulfillment of countless objectives and requirements.

By way of example, the prior art discloses in U.S. Pat. No. 3,945,046 a flexible knee support.

U.S. Pat. No. 5,107,824 discloses an anatomically correct knee brace hinge.

U.S. Pat. No. 5,139,015 discloses a knee support wrap for lifting weights.

U.S. Pat. No. Des. 331,805 discloses the design of a knee support.

U.S. Pat. No. 5,221,252 discloses an adjustable knee support.

In this respect, the multi-angle knee support according to the present invention substantially departs from the conventional concepts and designs of the prior art, and in doing so provides an apparatus primarily developed for the purpose of providing physical support to the knee of a wearer in a manner to simulate the support normally provided through ligaments.

Therefore, it can be appreciated that there exists a continuing need for new and improved multi-angle knee supports which can be used to provide physical support to the knee of a wearer in a manner to simulate the support normally provided through ligaments. In this regard, the present invention substantially fulfills this need.

SUMMARY OF THE INVENTION

In view of the foregoing disadvantages inherent in the known types of devices to be worn at the joint of a person to provide physical support to the joint now present in the prior art, the present invention provides an improved multi-angle knee support. As such, the general purpose of the present invention, which will be described subsequently in greater detail, is to provide a new and improved multi-angle knee support and method which has all the advantages of the prior art and none of the disadvantages.

To attain this, the present invention essentially comprise a new and improved multi-angle knee support comprising, in combination, an upper adjustment sleeve fabricated of a flexible elastic plastic material, preferably neoprene, the upper sleeve being fabricated in a loop-type configuration with free ends, pile-type fasteners secured to the free ends of the upper sleeve; a lower adjustment sleeve fabricated of an flexible elastic plastic material, preferably neoprene, the lower sleeve being fabricated in a loop-type configuration with free ends, pile-type fasteners secured to the free ends of the lower sleeve; two pair of primary ligament imitation strips, each such strip having an upper end and a lower end, each strip being fabricated of a plastic elastic material, preferably neoprene, each of the strips including therein a plurality of strands of flexible metallic material, preferably steel, to render the strips of limited elasticity, the strips being coupled at their upper ends to the upper sleeve at closely spaced points and coupled at their lower ends to the lower sleeve at closely spaced points beneath the upper spaced points, each strip being coupled to the upper and lower strips at the anterior face of the joint of a wearer and wrapped between about 270 and 360 degrees, in opposite directions, between the upper and lower sleeves to encompass the joint of the wearer; and a pair of secondary vertical ligament imitation strips, each such strip having an upper end and a lower end, each strip being fabricated of a plastic elastic material, preferably neoprene, each of such strips including therein a plurality of strands of flexible metallic material, preferably steel, to render the strips of limited elasticity, such strips being coupled between the upper and lower sleeves spaced from the points of coupling of the primary ligament imitation strips.

There has thus been outlined, rather broadly, the more important features of the invention in order that the detailed description thereof that follows may be better understood and in order that the present contribution to the art may be better appreciated. There are, of course, additional features of the invention that will be described hereinafter and which will form the subject matter of the claims appended hereto.

In this respect, before explaining at least one embodiment of the invention in detail, it is to be understood that the invention is not limited in its application to the details of construction and to the arrangements of the components set forth in the following description or illustrated in the drawings. The invention is capable of other embodiments and of being practiced and carried out in various ways. Also, it is to be understood that the phraseology and terminology employed herein are for the purpose of descriptions and should not be regarded as limiting.

As such, those skilled in the art will appreciate that the conception, upon which this disclosure is based, may readily be utilized as a basis for the designing of other structures, methods and systems for carrying out the several purposes of the present invention. It is important, therefore, that the claims be regarded as including such equivalent constructions insofar as they do not depart from the spirit and scope of the present invention.

Further, the purpose of the foregoing abstract is to enable the U.S. Patent and Trademark Office and the public generally, and especially the scientists, engineers and practitioners in the art who are not familiar with patent of legal terms or phraseology, to determine quickly from a cursory inspection the nature and essence of the technical disclosure of the application. The abstract is neither intended to define the invention of the application, which is measured by the claims, nor is it intended to be limiting as to the scope of the invention in any way.

It is therefore an object of the present invention to provide new and improved multi-angle knee supports which have all the advantages of the prior art devices to be worn at the joint of a person to provide physical support to the joint and none of the disadvantages.

It is another object of the present invention to provide new and improved multi-angle knee supports which may be easily and efficiently manufactured and marketed.

It is further object of the present invention to provide new and improved multi-angle knee supports which are of durable and reliable constructions.

An even further object of the present invention is to provide new and improved multi-angle knee supports which are susceptible of a low cost of manufacture with regard to both materials and labor, and which accordingly are then susceptible of low prices of sale to the consuming public, thereby making such multi-angle knee supports economically available to the buying public.

Still yet another object of the present invention is to provide new and improved multi-angle knee supports which provide in the apparatuses and methods of the prior art some of the advantages thereof, while simultaneously overcoming some of the disadvantages normally provided through ligaments associated therewith.

Still another object of the present invention is to provide physical support to the knee of a wearer in a manner to simulate the support normally provided through ligaments.

Lastly, it is an object of the present invention to provide a new and improved multi-angle knee support comprising an upper adjustment sleeve fabricated of a flexible elastic plastic material, the upper sleeve being fabricated in a loop-type configuration with free ends, pile-type fasteners secured to the free ends of the upper sleeve; a lower adjustment sleeve fabricated of an flexible elastic plastic material, the lower sleeve being fabricated in a loop-type configuration with free ends, pile-type fasteners secured to the free ends of the lower sleeve; and a plurality of ligament imitation strips coupled between the upper and lower sleeves.

These together with other objects of the invention, along with the various features of novelty which characterize the invention, are pointed out with particularity in the claims annexed to and forming a part of this disclosure. For a better understanding of the invention, its operating advantages and the specific objects attained by its uses, reference should be had to the accompanying drawings and descriptive matter in which there is illustrated preferred embodiments of the invention.

BRIEF DESCRIPTION OF THE DRAWINGS

The invention will be better understood and objects other than those set forth above will become apparent when consideration is given to the following detailed description thereof. Such description makes reference to the annexed drawings wherein.

The same reference numerals refer to the same parts through the various Figures.

DESCRIPTION OF THE PREFERRED EMBODIMENT

Figures 1, 2:
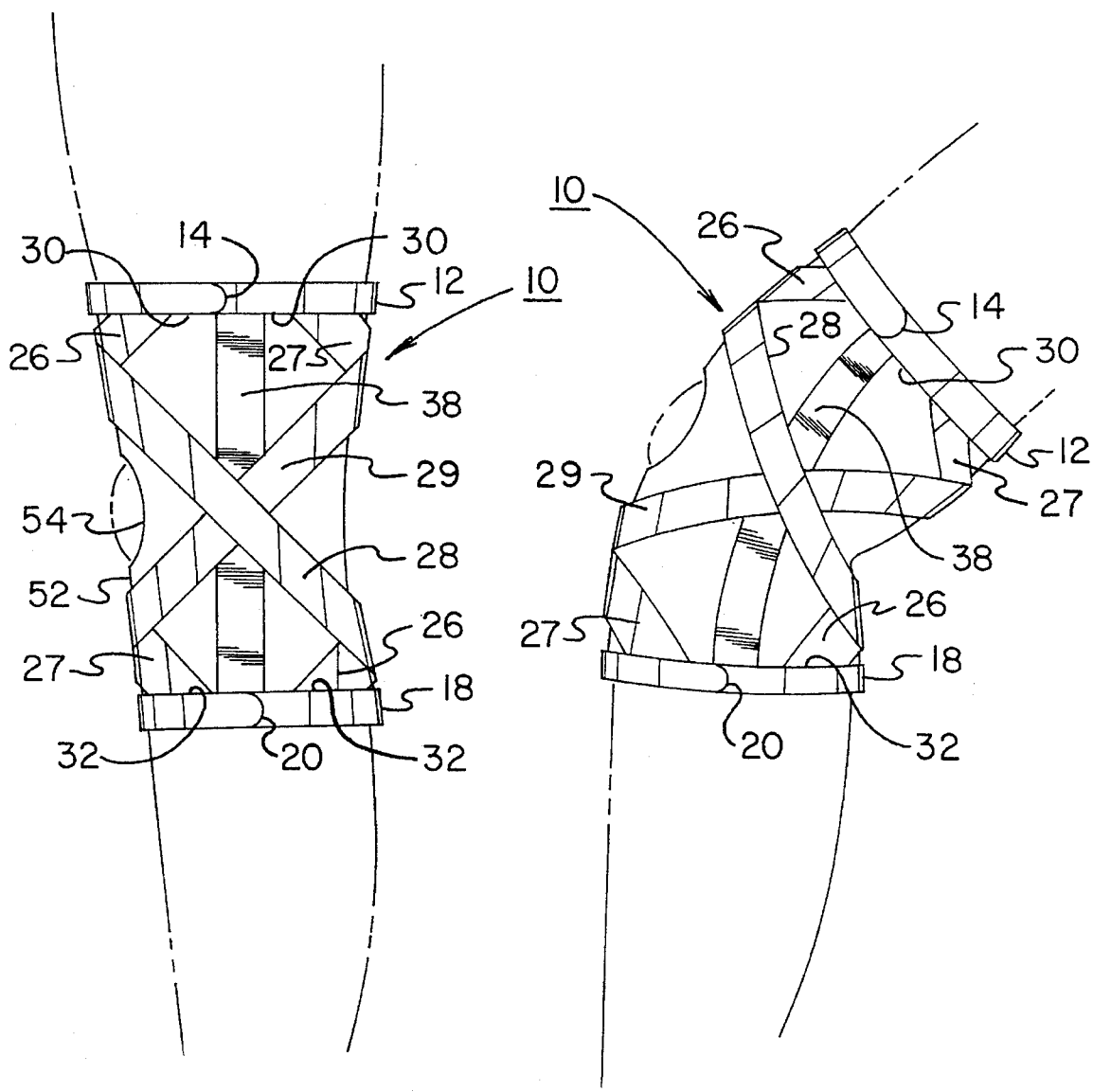
FIG. 1 is a side elevational view of the preferred embodiment of the multi-angle knee support constructed in accordance with the principles of the present invention.
FIG. 2 is a side elevational view similar to FIG. 1 but illustrating the device mounted on a knee which is bent.
Figure 3:
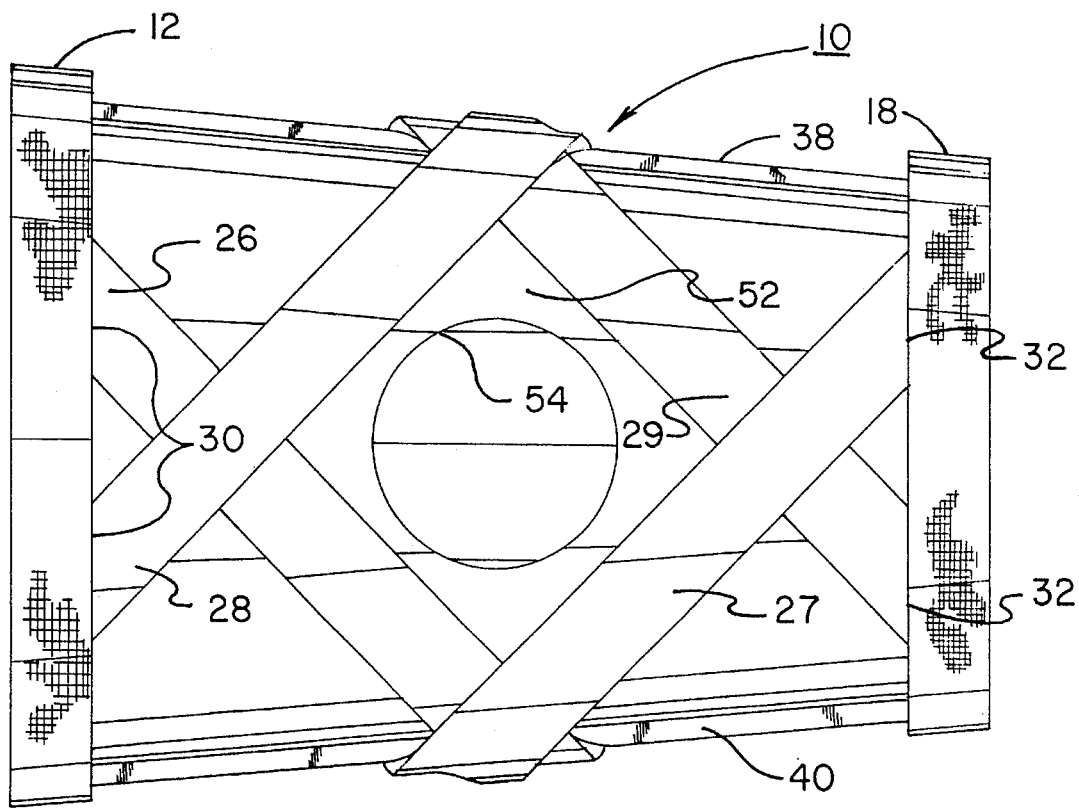
FIG. 3 is a front elevational view of the device shown in FIGS. 1 and 2.
Figure 4:
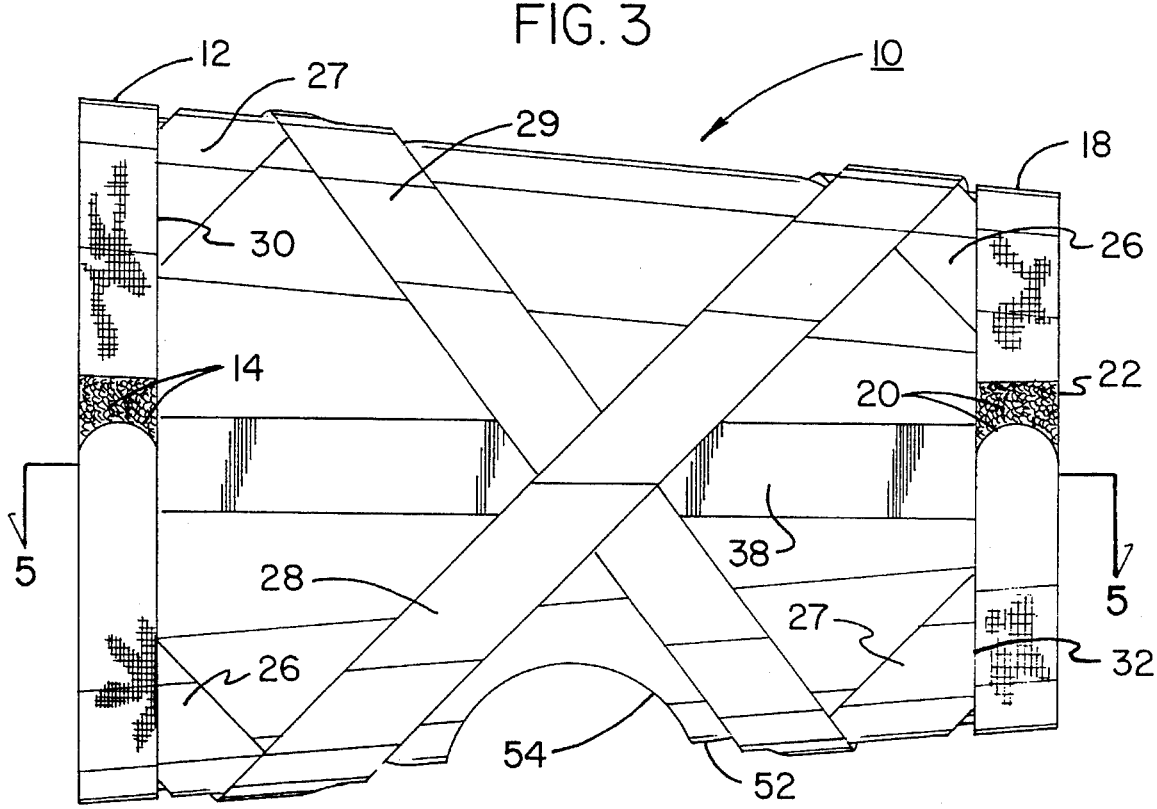
FIG. 4 is a side elevational view of the device shown in FIG. 3.
Figure 5:
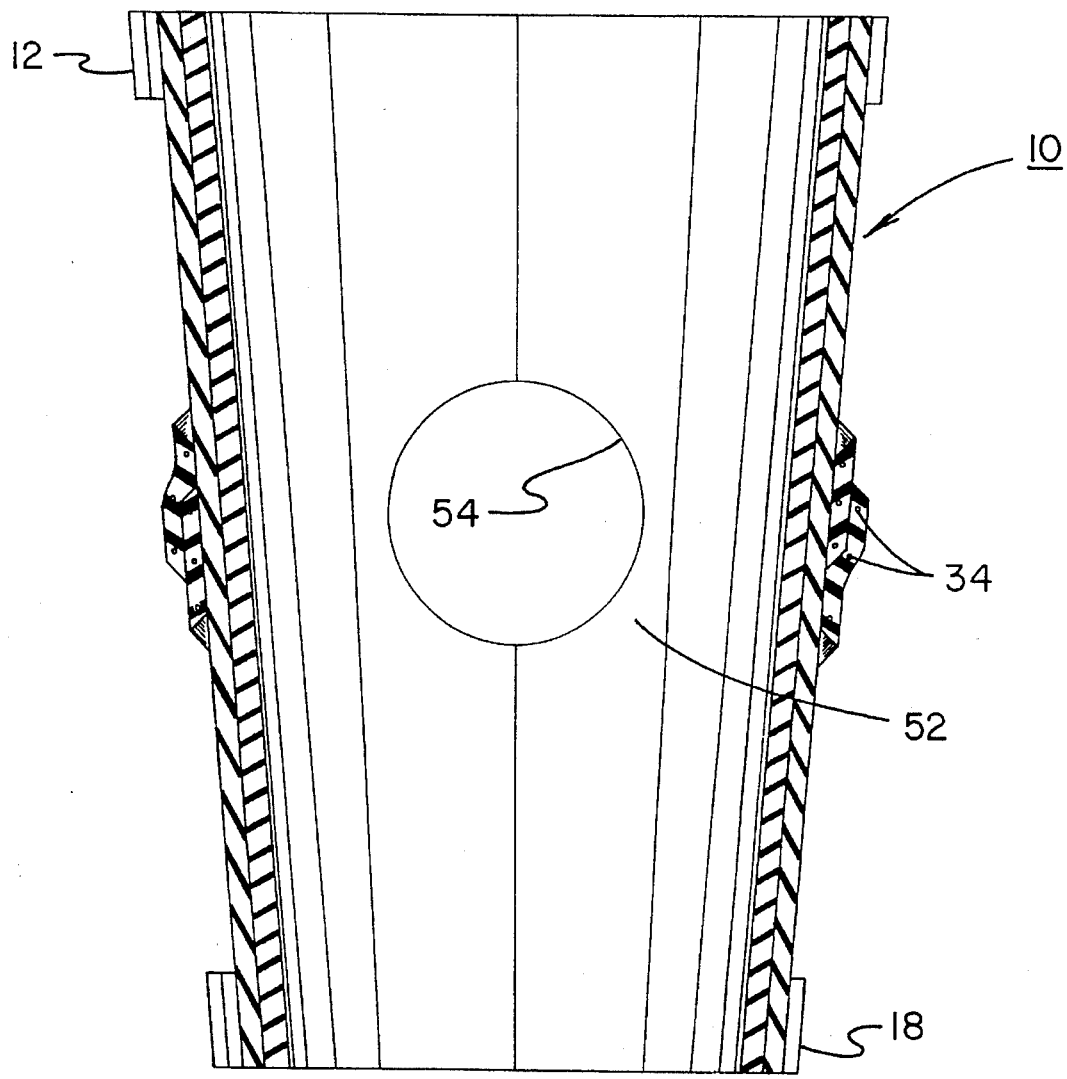
FIG. 5 is a cross-sectional view taken along lines 5—5 of FIG. 4.
Figure 6:
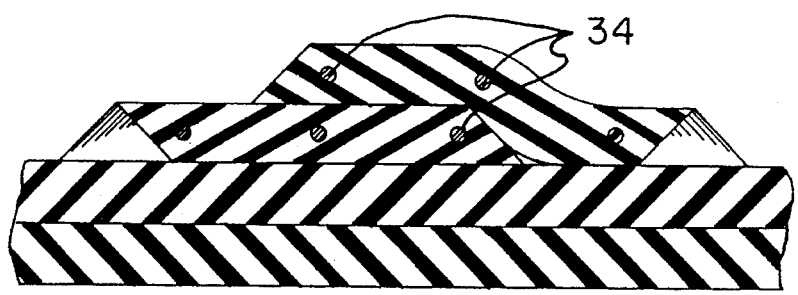
FIG. 6 is a close-up cross-sectional view of the interaction between the primary ligament imitation strips shown in FIG. 5.
Figure 8:
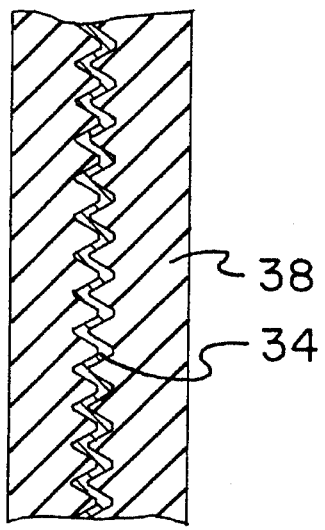
FIG. 8 is a cross-sectional view taken along lines 8—8 of FIG. 7.
Figure 7:
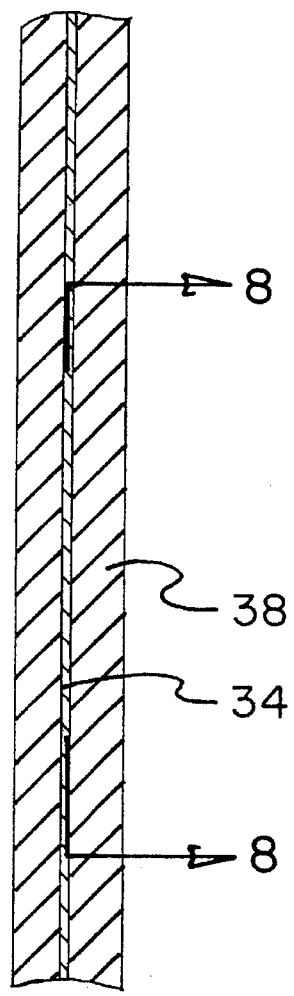
FIG. 7 is a cross-sectional view of the secondary vertical ligament imitation strip.
Figure 9:
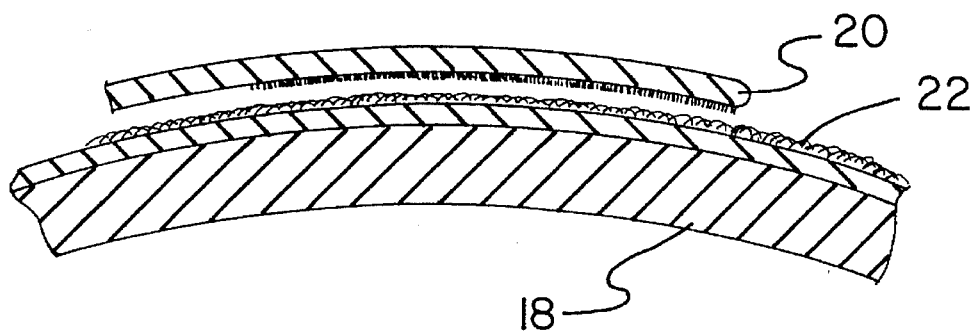
FIG. 9 is a cross-sectional view of the pile-type fastener of a sleeve.

With reference now to the drawings, and in particular to FIGS. 1 through 9 thereof, the preferred embodiment of the new and improved multi-angle knee support embodying the principles and concepts of the present invention and generally designated by the reference numeral 10 will be described.

The present invention, the new and improved multi-angle knee support is a system comprised of a plurality of components. The components in their broadest context include an upper adjustment sleeve, a lower adjustment sleeve, a pair of primary ligament strips and a pair of vertical ligament imitation strips. Each of the individual components is specifically configured and correlated one with respect to the other to attain the desired objectives.

Central components of the system 10 of the present invention include a pair of adjustment sleeves including an upper adjustment sleeve 12. The upper adjustment sleeve includes an anterior side and a posterior side. Such sleeve is fabricated of a flexible elastic plastic material. Neoprene is the preferred material. The upper sleeve is fabricated in a loop type configuration. It is also provided with free ends 14. Pile type fasteners are secured to the free ends of the upper sleeve for securing it to a wearer above the knee.

Next provided is a lower adjustment sleeve 18, similar in construction to the upper adjustment sleeve. The lower adjustment sleeve includes an anterior side and posterior side. It also is fabricated of a flexible elastic plastic material. The preferred material is neoprene. The lower sleeve is fabricated in a loop type configuration. It also has free ends 20. Pile type fasteners 22 are secured to the free ends of the lower sleeves. It is intended to be positioned beneath the knee of a wearer.

Coupling the upper and lower adjustment sleeves are a pair of primary ligament imitation strips 26, 28. Each such strip has an upper end 30 and a lower end 32. Each strip is fabricated of a plastic elastic material. Neoprene is the preferred material. Each of the strips includes therein a plurality of strands 34 of flexible metallic material. The preferred metallic material is steel in thin strands to render it flexible but essentially inextensible. Such strips have limited elasticity.

Both the strips are coupled at their upper ends to the anterior side of the upper sleeve at closely spaced points. Both the strips are coupled at their lower ends to the posterior side of the lower sleeve, again at closely spaced points, but beneath the upper spaced points and in generally vertical alignment therewith. The strips are wrapped between 270 degrees and 360 degrees with respect to the central axis of the support and knee when the wearer is in an erect position. They are wrapped between the upper and lower sleeves to encompass the joint of a user.

Additionally coupling the upper and lower adjustment sleeves are a second pair of primary ligament imitation strips 27, 29. Each such strip has an upper and lower ends like the first pair. Each second strip is fabricated of material as the first strips. Both the second strips are coupled at their upper ends to the posterior side of the upper sleeve and at their lower ends to the anterior side of the lower sleeve, again at closely spaced points about 180 degrees from the first strips and are wrapped between 270 degrees and 360 degrees with respect to the central axis of the support and knee when the wearer is in an erect position. They are wrapped between the upper and lower sleeves to encompass the joint of a user.

Additionally, there is also provided a pair of vertical ligament imitation strips 38, 40. Such strips are coupled between the upper and lower sleeves. They extend from points spaced from the points of coupling of the primary ligament imitation strips.

Each such strip has an upper end and a lower end. Each strip is fabricated of a plastic elastic material. Neoprene is the preferred material. Each of the strips includes therein a plurality of strands 34 of flexible metallic material. The preferred metallic material is steel in thin strands to render it flexible but essentially inextensible. Such strips have limited elasticity.

Lastly, a conventional tubular elastic sheath 52, preferably of neoprene, is provided for positioning around a wearer's knee. Such sheath is located in contact with the wearer, beneath the upper and lower sleeves and beneath the strips as described above so as to provide additional support. A knee opening 54 is located centrally thereof for maximum flexibility of a wearer's knee during use.

The present invention provides support for a person's knee without restricting motion as a rigid knee brace would. It is designed to mimic the support angles and characteristics of the actual ligaments in an around the knee.

The present invention consists of a neoprene sleeve similar to those worn over an injured knee, two adjusting strips made of pile type hook and loop material and ligament imitation strips (LIS) that are secured to the sleeve. The LIS are made from neoprene with longitudinal metal threads embedded in them. The neoprene provides the elasticity necessary for the LIS to stretch as do normal ligaments. These metal threads, which are slack when the LIS is at its unstretched length, provide the stopping or end point when they are stretched to a predetermined length, similar to the action of a real ligament. To replicate actual ligaments the LIS are positioned and secured on the neoprene sleeve in patterns similar to those around the human knee. Some of the LIS are placed in a crossing design in the front and the back of the sleeve, to support the functioning of the anterior and posterior cruciate ligaments. Two vertical LIS, one on each side of the knee, help support the functions of the medial and lateral collateral ligaments.

The present invention is pulled over the problem knee and secured in place with the hook and look material strips located around the top and bottom of the support. With this device in place, the person can perform the natural range of motion of the knee joint, but undesirable degrees of motion will be limited.

The ligament imitation strips can also be used in support devices for other joints, for example, ankles, elbow and shoulders. The present invention should be appreciated by professional and amateur athletes as well as people for people with joint stability problems.

As to the manner of usage and operation of the present invention, the same should be apparent from the above description. Accordingly, no further discussion relating to the manner of usage and operation will be provided.

With respect to the above description then, it is to be realized that the optimum dimensional relationships for the parts of the invention, to include variations in size, materials, shape, form, function and manner of operation, assembly and use, are deemed readily apparent and obvious to one skilled in the art, and all equivalent relationships to those illustrated in the drawings and described in the specification are intended to be encompassed by the present invention.

Therefore, the foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

What is claimed as being new and desired to be protected by Letters Patent of the United States is as follows:

1. A new and improved multi-angle knee support comprising, in combination:

an upper adjustment sleeve fabricated of a flexible elastic plastic material, the upper sleeve comprising a posterior side and an anterior side and being fabricated in a loop configuration with free ends, pile fasteners secured to the free ends of the upper sleeve;

a lower adjustment sleeve fabricated of a flexible elastic plastic material, the lower sleeve comprising a posterior side and an anterior side and being fabricated in a loop configuration with free ends, pile fasteners secured to the free ends of the lower sleeve;

two pair of primary ligament imitation strips, each such strip having an upper end and a lower end, each strip being fabricated of a plastic elastic material, each of the strips including therein a plurality of strands of flexible metallic material, to render the strips of limited elasticity, the strips including a first pair of strips having a first end coupled to the anterior side of the upper sleeve and a second end coupled to the posterior side of the lower sleeve and a second pair of strips having a first end coupled to the posterior side of the upper sleeve and a second end coupled to the anterior side of the lower sleeve, wherein the strips are adapted to be wrapped between about 270 and 360 degrees in opposite directions between the upper and lower sleeves to thereby encompass the joint of a wearer; and a pair of secondary vertical ligament imitation strips, each such strip having an upper end and a lower end, each strip being fabricated of a plastic elastic material, each of such strips including therein a plurality of strands of flexible metallic material, to render the strips of limited elasticity, such strips being coupled between the upper and lower sleeves spaced from the points of coupling of the primary ligament imitation strips.

2. A multi-angle knee support comprising, in combination:

an upper adjustment sleeve fabricated of a flexible elastic plastic material, the upper sleeve being fabricated in a loop configuration with free ends, pile fasteners secured to the free ends of the upper sleeve;

a lower adjustment sleeve fabricated of an flexible elastic plastic material, the lower sleeve being fabricated in a loop configuration with free ends, pile fasteners secured to the free ends of the lower sleeve;

a plurality of primary ligament imitation strips coupled between the upper and lower sleeves, each of such strips adapted to be wrapped between 270 and 360 degrees in opposite directions between the upper and lower sleeves to thereby encompass a joint of a wearer; and a plurality of secondary vertical ligament imitation strips coupled between the upper and lower sleeves spaced from the points of coupling of the primary ligament imitation strips.

3. A multi-angle knee support comprising:

an upper adjustment sleeve fabricated of a flexible elastic material, the upper sleeve being fabricated in a loop configuration with free ends, pile fasteners secured to the free ends of the upper sleeve;

a lower adjustment sleeve fabricated of an flexible elastic plastic material, the lower sleeve being fabricated in a loop configuration with free ends, pile fasteners secured to the free ends of the lower sleeve; and at least one pair of primary ligament imitation strips, each such strip having an upper end and a lower end, each strip being fabricated of a plastic material, each of the strips including therein a plurality of strands of flexible metallic material, to render the strips of limited elasticity, the strips including a first pair or strips having a first end coupled to the anterior side of the upper sleeve and a second end coupled to the posterior side of the lower sleeve and a second pair of strips having a first end coupled to the posterior side of the upper sleeve and a second end coupled to the anterior side of the lower sleeve, wherein the strips are adapted to be wrapped between about 270 and 360 degrees, in opposite directions between the upper and lower sleeves to thereby encompass the joint of a wearer.

\* \* \* \* \*